United States Patent [19]
Young et al.

[11] Patent Number: 5,531,112
[45] Date of Patent: Jul. 2, 1996

[54] FLUID HOLDUP TOOL FOR DEVIATED WELLS

[75] Inventors: Allen R. Young, Arlington; Jerry L. Davidson, Burleson; Edward Baltazar, Keene, all of Tex.

[73] Assignee: Computalog U.S.A., Inc., Fort Worth, Tex.

[21] Appl. No.: 246,842

[22] Filed: May 20, 1994

[51] Int. Cl.$^6$ .......................... F21B 47/00; G01R 27/22; G01N 11/00; G01V 1/40
[52] U.S. Cl. .......................... 73/152; 73/155; 73/61.46; 175/50; 166/66; 166/117.7
[58] Field of Search .................. 73/152, 155, 61.46, 73/61.49; 175/50; 166/66, 117.7

[56] References Cited

U.S. PATENT DOCUMENTS

| | | | |
|---|---|---|---|
| 3,260,104 | 7/1966 | King, Jr. | 73/23 |
| 3,359,788 | 12/1967 | Colvin | 73/61.1 |
| 3,820,063 | 6/1974 | Sexton et al. | 340/18 LD |
| 3,982,606 | 9/1976 | Berry et al. | 181/102 |
| 4,116,045 | 9/1978 | Potter | 73/61.1 |
| 4,130,816 | 12/1978 | Vogel et al. | 340/15.5 BH |
| 4,159,638 | 7/1979 | Potter | 73/61.1 R |
| 4,293,933 | 10/1981 | Park et al. | 367/25 |
| 4,565,088 | 1/1986 | Crambes | 73/61.1 R |
| 4,876,672 | 10/1989 | Petermann et al. | 367/35 |
| 4,928,758 | 5/1990 | Siegfried, II | 166/66 |
| 4,974,446 | 12/1990 | Vigneaux | 73/155 |
| 5,083,452 | 1/1992 | Hope | 73/61 R |
| 5,220,826 | 6/1993 | Hompel et al. | 73/61.49 |
| 5,249,455 | 10/1993 | Cox | 73/61.44 |
| 5,260,667 | 11/1993 | Garcia-Golding et al. | 324/694 |

FOREIGN PATENT DOCUMENTS

0372598  6/1990  European Pat. Off. .

Primary Examiner—Hezron E. Williams
Assistant Examiner—J. David Wiggins
Attorney, Agent, or Firm—Mark W. Handley; Andrew J. Dillon

[57] ABSTRACT

A production logging tool is provided for use within a well to determine fluid holdup of a multiphase fluid flow within the well. The production logging tool includes a plurality of sensors secured within a plurality of arms which radially extend from a tool housing to points distal from the tool housing. A plurality of sensors are included within the plurality of arms for detecting variations in fluid properties attributable to different flow constituents of the multiphase fluid flow along a path which circumscribes an exterior of the tool housing. The plurality of arms are rotated about the tool housing for moving these sensors through the path in order to ensure that the volumetric proportions of the different flow constituents of the multiphase fluid flow are accurately detected in highly deviated and in horizontal wells.

17 Claims, 11 Drawing Sheets

FLUID HOLDUP TOOL FOR DEVIATED WELLS

BACKGROUND OF THE INVENTION

1. Field of the Invention

This invention relates in general to logging tools for detecting parameters of fluid flows, and in particular to a logging tool for detecting flow parameters of multiphase fluid flow.

2. Description of the Prior Art

Prior art logging tools have been utilized for detecting flow parameters for different types of fluid flows. For example, well logging tools are frequently used within producing oil and gas wells for detecting flow rates for different fluid flow components being produced within petroleum wells. Prior art production logging tools have frequently included spinner types of flowmeters having an impeller which is caused to rotate when immersed within a flowstream. Such flowmeters include fullbore flowmeters and deflector flowmeters. Additionally, production logging tools have included other tools for detecting downhole densities and pressures of production fluids.

Prior art water holdup meters have been provided by utilizing well logging tools which work by detecting the dielectric constant of the produced fluids. This particular type of water holdup tool operates under the principle that different fluids have different dielectric constants. Typically, electrodes are provided within a tool housing, and the electrodes are disposed about a longitudinal axis of a logging tool. The electrodes are connected to a capacitance measurement means which detects the net dielectric constant for fluids flowing within the central portion of a well immediately about the tool housing.

This type of prior art logging tool has several limitations. One is that the tool does not work properly if the water holdup becomes so high that the water phase becomes continuous. In that case, such as a flow of a mixture of oil and water with the oil dispersed as bubbles in a continuous water medium, the high conductivity of the water masks varying dielectric effects that are attributable to the changes in the volumetric fraction of the oil included within the oil and water mixture. Another problem occurs in that only the dielectric constant of the central portion of the well is measured. Very often flow will vary across a section of the well, especially in deviated wells. In fact, in highly deviated wells, such as horizonal wells, the fluid flow may become stratified across a cross-sectional area of the well. This may result in prior art fluid holdup tools detecting only a small portion of the stratified flow, such as only one phase, and not the other portions of the flow of produced fluids.

Further, different flow patterns may be present both in vertical flow and horizontal flow. In horizontal flow, very often bubble flow, and elongated bubble flow will occur. Additionally, stratified flow, wave flow, slug flow, annular and annular mist flow, and dispersed froth flow may occur depending on the different flow parameters and flow velocities encountered. Vertical flow patterns may also include bubble flow, froth flow, annular, annular mist flow, and slug flow. These different flow patterns occur depending on the velocities, the cross-sectional diameter, and other such parameters affecting flow rate. Typically the volumetric proportions which occur at downhole well conditions are much different than those that occur further uphole, as well as on the surface. This is affected by the amount of gas which stays in solution and other such similar type of phenomenon.

Typically, different densities, frictional parameters and different phases for different constituents of segregated multiphase fluid flow result in different flow rates for the different constituents. For example, in a segregated, multiphase flow in a producing well having flow constituents which consist of oil, gas and water, the gas phase may flow faster than the oil phase, which may flow faster than a water phase. In fact, in some sections of wells having multiple zones of production, one phase may flow in an opposite direction within the well to that of a net flow of fluids. When annular type of flow segregation occurs, such as with slug, annular mist, and froth flow, only the flow occurring within the central portion of a cross-sectional area of a well is detected. Very often the flow occurring around an outer circumference of the well is not detected by prior art well logging tools, such as the capacitance type of water holdup meter discussed above.

SUMMARY OF THE INVENTION

It is one objective of the present invention to provide a production logging tool for use in detecting flow parameters at points which are distal from a tool housing.

It is another objective of the present invention to provide a production logging tool for detecting fluid holdup of a multiphase fluid flow within a producing oil and gas well.

It is yet another objective of the present invention to provide a production logging tool for detecting variations in fluid properties attributable to different flow constituents of a multiphase fluid flow at a plurality of points which are distal to a tool housing for the production logging tool.

It is yet still another objective of the present invention to provide a production logging tool for detecting flow parameters of a multiphase fluid flow in highly deviated wells for determining the volumetric proportions of different flow constituents of the multiphase fluid flow at a plurality of measurement points disposed about the cross-sectional area of the well, wherein the measurement points are distal from a central portion of the well.

It is further still another objective of the present invention to provide a production logging tool having sensors which are disposed distal from the tool housing and which are rotated about a circumference of the well for detecting variations in fluid properties attributable to different flow constituents of the multiphase fluid flow at a plurality of measurement points located about the circumference.

The above objectives are achieved as is now described. A production logging tool is provided for use within a well to determine fluid holdup of a multiphase fluid flow within the well. The production logging tool includes a plurality of sensors secured within a plurality of arms which radially extend from a tool housing to points distal from the tool housing. A plurality of sensors are included within the plurality of arms for detecting variations in fluid properties attributable to different flow constituents of the multiphase fluid flow along a path which circumscribes an exterior of the tool housing. The plurality of arms are rotated about the tool housing for moving these sensors through the path in order to ensure that the volumetric proportions of the different flow constituents of the multiphase fluid flow are accurately detected in highly deviated and in horizontal wells.

In the preferred embodiment of the present invention, three arms radially extend from the tool housing for disposing three sensors at three equally spaced points about a circumference about the exterior of the flowstream. The sensors may either be of one type, or combination of various sensor types. Such sensors utilized may include electrical resistivity sensors, thermal conductivity sensors, or acoustic impedance sensors. An encoder means determines the angular rotation of the sensors about the tool housing for correlating sensor readings with various sensor positions about the tool housing. A caliper detection means determines when the plurality of arms encounter various flow restrictions.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

Figures 1, 2:
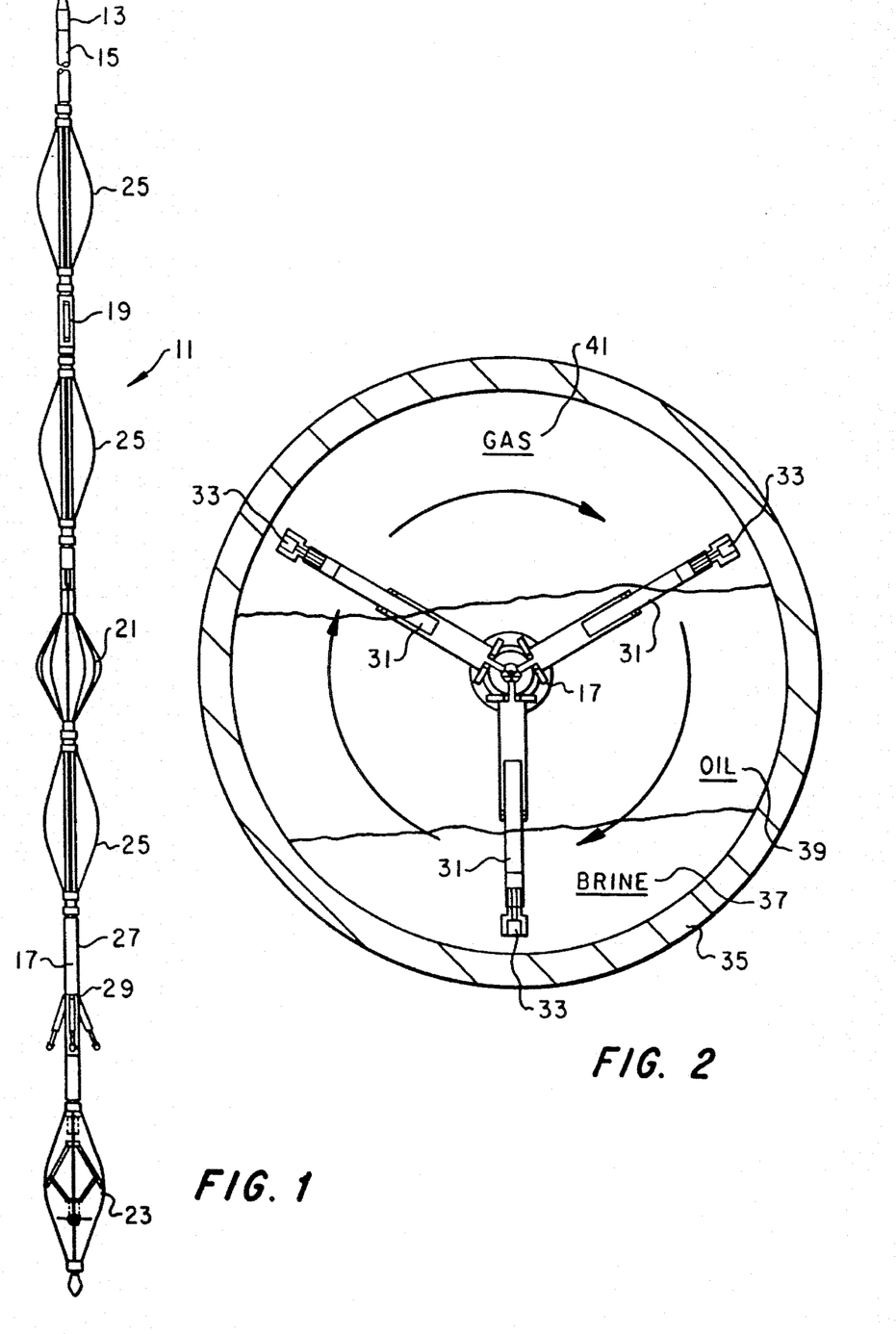
FIG. 1 is a perspective view of a production logging tool string which includes the fluid holdup tool of the present invention.
FIG. 2 is a cross-sectional view of a casing within a deviated well within which the fluid holdup tool of the present invention is being operated to measure relative volumes for flow constituents of production fluids flowing in a multiphase fluid flow passing within the casing.

With reference to FIG. 1, a perspective view depicts production logging tool string 11 for use to analyze a multiphase fluid flow within a well. Tool string 11 includes cable head 13, telemetry section 15, density tool 19, deflector flowmeter 21, and full bore flowmeter 23. Bow spring centralizers 25 are included along tool string 11 for centering tool string 11 within a well. Included within production logging tool string 11 of the present invention is fluid holdup tool 17, which includes upper section 27 and lower section 29. Three caliper arms 31 radially extend from lower section 29 of fluid holdup tool 17 of the present invention.

Referring now to FIG. 2, a sectional view depicts fluid holdup tool 17 within a well. Arms 31 radially extend from fluid holdup tool 17 and include sensors 33. Holdup tool 17 is shown within casing 35, which is depicted herein for a deviated well, such as a horizontal well. Production fluids flowing within casing 35 include brine 37, oil emulsions 39, and gas 41. Arms 31 and sensors 33 are rotated in the direction of arrow 43 for depicting the volumetric proportions of flow constituents 39, 41 and 43.

Figures 3A, 3B:
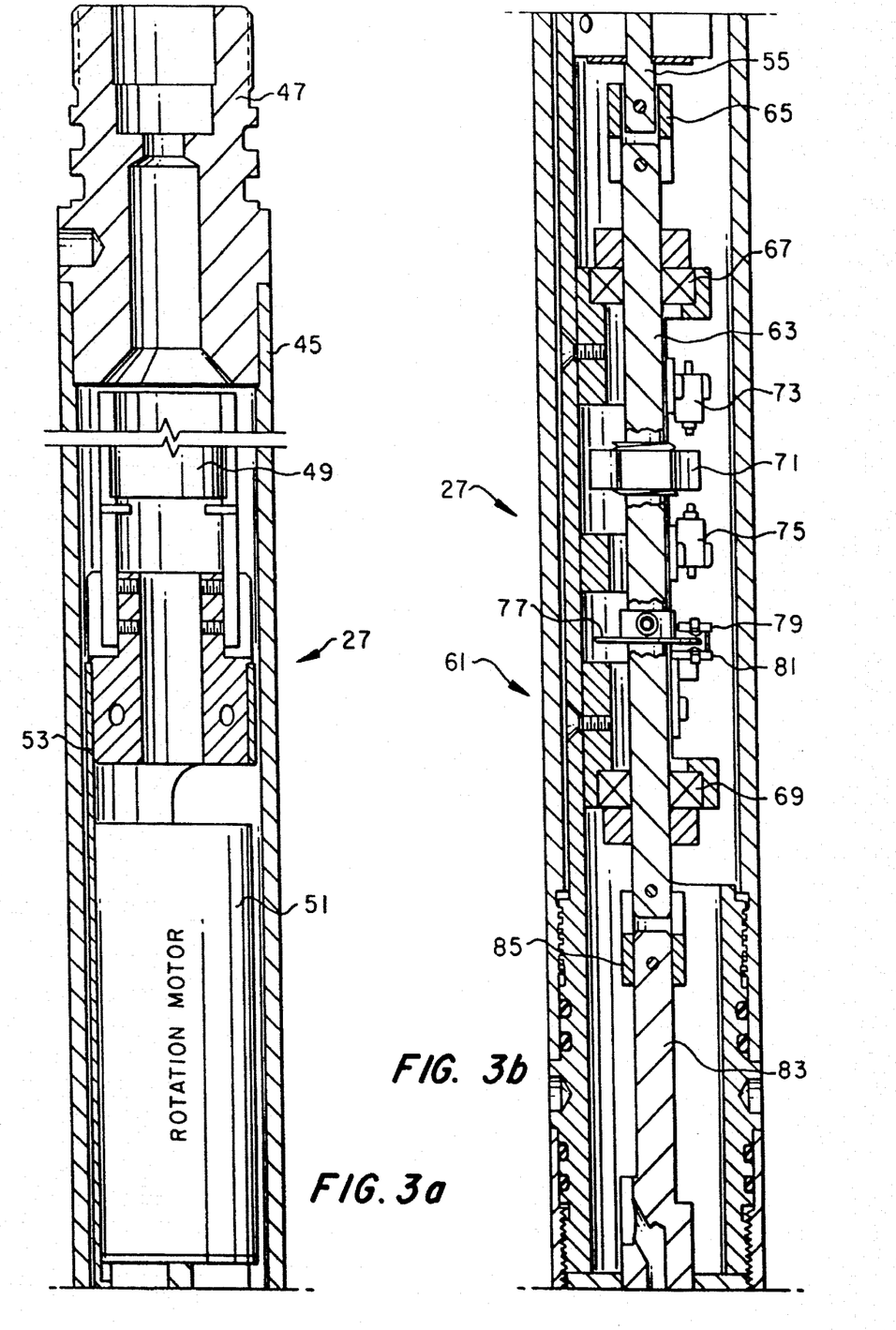
FIGS. 3a–3c together comprise a cross-sectional view depicting an upper section of the fluid holdup tool of the present invention.
Figures 3C, 4A:
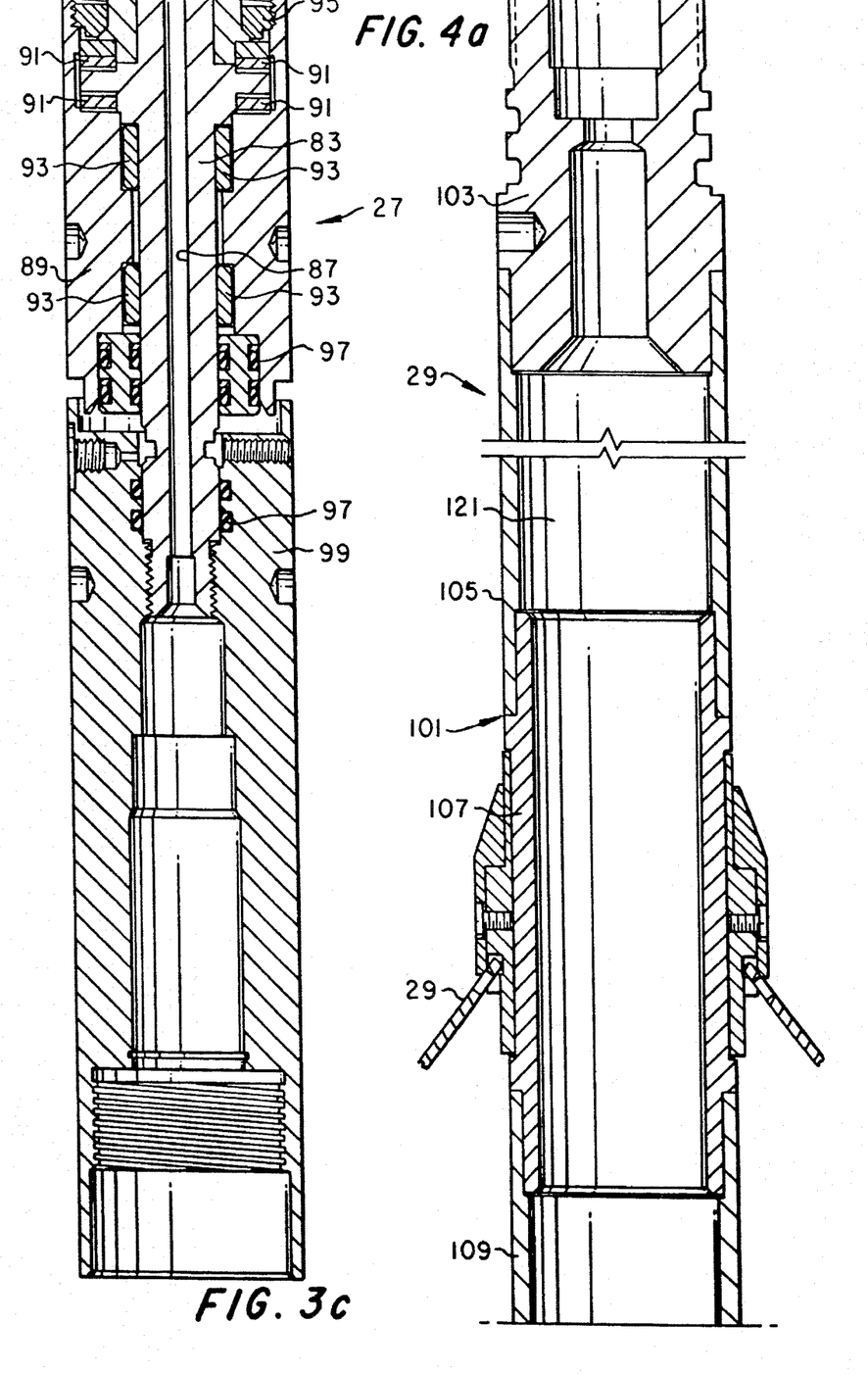
FIGS. 4a–4f together comprise a longitudinal section view of a lower section of the fluid holdup tool of the present invention.

With references to FIG. 3a–3c, a longitudinal section view depicts upper section 27 of fluid holdup tool 17. Upper section 27 includes upper pressure housing 45. Connector 47 extends from the upper end of housing 45 for securing tool 17 within a tool string, such as tool string 11 shown in FIG. 1. Electronics section 49 is disposed within the top of upper pressure housing 45. Rotation motor 51 is secured within housing 45 by motor bracket means 53. Output shaft 55 extends from motor 51 to provide a rotation means. Rotary encoder section 61 extends below rotation motor 51 to provide a means for detecting rotation of shaft 63. Shaft 63 is secured to output shaft 55 by shaft coupling 65. Bearings 67 and 69 support shaft 63 within housing 45. Floating nut 71 is secured to shaft 63 between limit switches 73 and 75. Encoder wheel 77 is secured to shaft 63 for rotating therewith between L.E.D. 79 and photodiode 81. Encoder wheel 77 includes slots, or holes, so that L.E.D. 79 will pass light through the slots in encoder wheel 77 and to photodiode 81 as encoder wheel 77 rotates. Photodiode 81 emits electric pulses in response to receiving light pulses from L.E.D. 79 which pass through the slots of encoder wheel 77. The electric pulses from photodiode 81 correspond to angular rotation of shaft 63, which corresponds to rotation of lower section 29 of fluid holdup tool 17.

Shaft 83 is coupled to shaft 63 by shaft coupling 85. Shaft 83 includes wireway 87 which extends therein for passing wiring between upper section 27 and lower section 29 of fluid holdup tool 17. Shaft 83 is rotatably supported within bearing section 89 of housing 45 by bearings 91 and bearings 93. Lock nut 95 threadingly engages an interior of bearing section 89 for retaining bearings 91 and shaft 83 within bearing section 89. Seals 97 seal between shaft 83 and bearing section 89, and shaft 83 and housing coupling 99. Housing coupling 99 is threadingly secured to the lower end of shaft 83 for rotating therewith relative to bearing section 89 of upper housing 45. It should be noted that upper housing 45 is typically held in place by centralizers within the upper portions of a production logging string as housing coupling 99 and lower section 29 are rotated within a well by rotation motor 51. The lower end of housing coupling 99 is threaded and has a seal surface for securing to a lower section 29 of fluid holdup tool 17.

Referring now to FIGS. 4a–4f, a longitudinal section view depicts lower section Z9 of fluid holdup tool 17, with bull nose 117 secured to the lower end of lower section 29. Lower section 29 includes lower pressure housing 101. Connector 103 is secured in the upper end of housing 101 for connecting lower section 29 to upper section 27. Lower pressure housing 101 includes pressure sleeve 105, centralizer sleeve 107, pressure sleeve 109, pressure coupling 111, about which is secured at centralizer sleeve 113, and slotted sleeve 115. Bull nose 117 is depicted as secured in the lower end of fluid holdup tool 17 rather than density tool 19 for illustrative purposes in order to depict how tool 17 appears when not run above other components in a production logging tool string. In other embodiments of the present invention, a tool connection may be provided rather than bull nose 117 for connecting other tools to the lower end of fluid holdup tool 17, such as shown in tool string 11 of FIG. 1. Centralizer sleeves 107 and 113 rotatably support one of centralizers 29 about lower pressure housing 101 so that housing 101 may rotate therein as centralizer 29 is held stationary within a well.

Figure 4B:
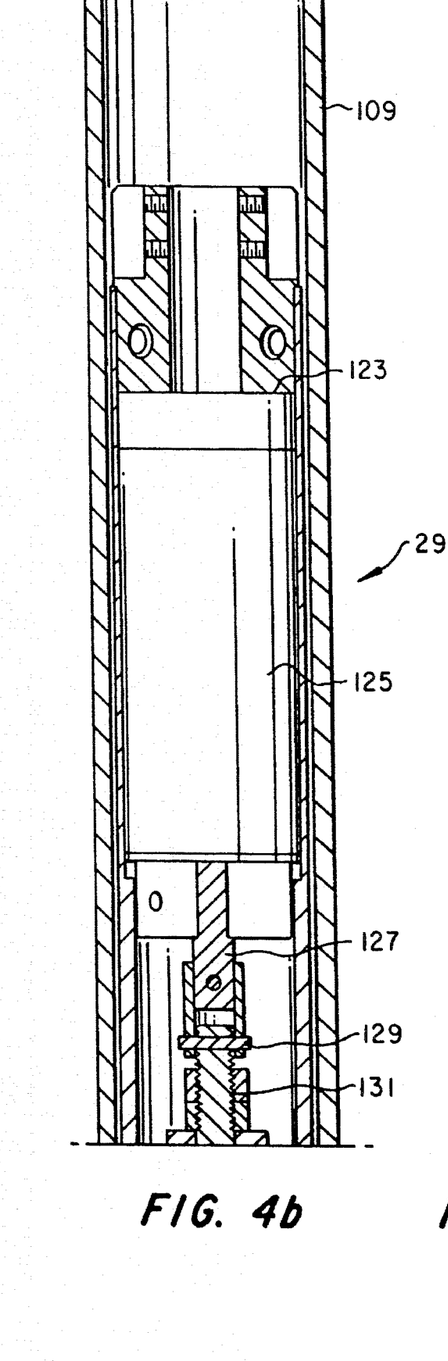

The upper end of housing 101 has electronics section 121 disposed therein. Motor bracket means 123 secures caliper motor 125 within housing 101. Output shaft 125, together with caliper motor 125, provides a caliper extension and retraction means. Shaft 131 is coupled to output shaft 127 by coupling 129. Bearing 133 supports shaft 101 within housing 101. Worm gear 135 is secured to the lower end of shaft 131 for moving therewith. Ball nut assembly 136 includes balls 137, bracket 138 and nut 140 for moving linearly, in a longitudinal direction within housing 101, as worm gear 135 is rotated by caliper motor 125.

Figure 4C:
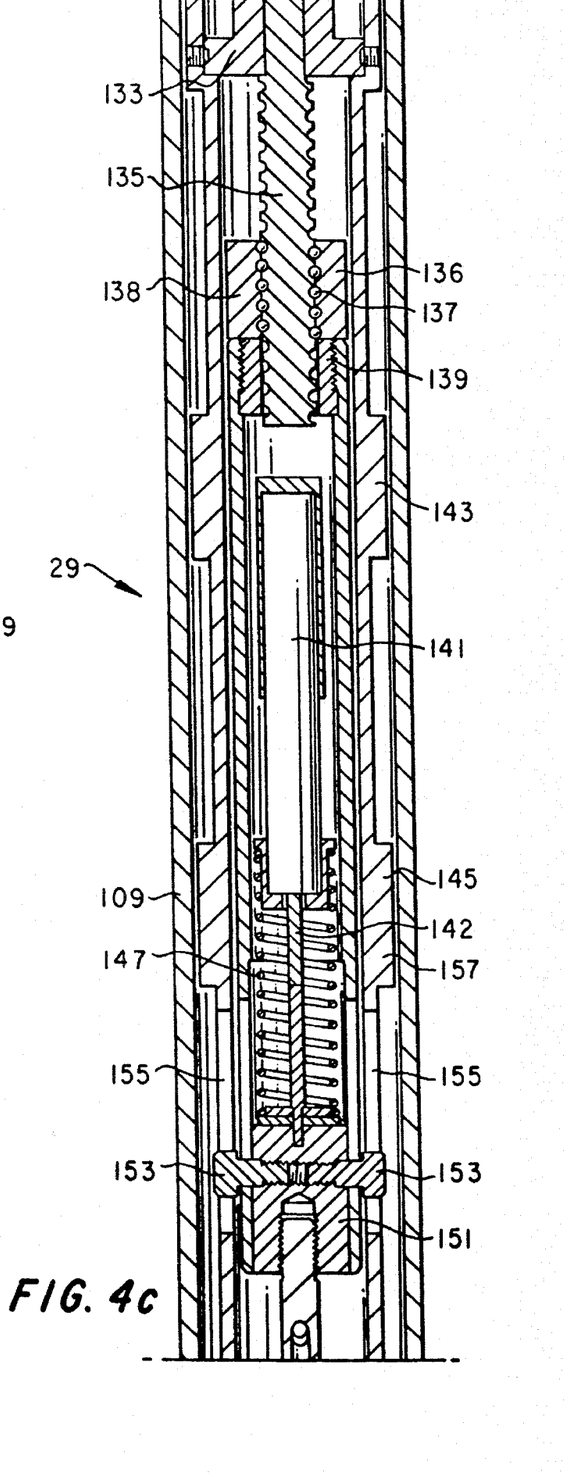

Linear variable differential transformer (LVDT) 141 having core 142 provides a means for determining the amount by which caliper arms 31 are extended during operation of fluid holdup tool 17. Shoulders 143 and 145 are provided to secure limit switches within housing 101 to limit opening and closing of caliper arms 31. Bias spring 147 extends between coupling 151 and retaining bracket 145 for biasing coupling 151 towards the lower end of lower pressure housing 101. Bias spring 147 may be compressed when caliper arms 31 encounter a restriction within a well. Lugs 153 extend from coupling 151 within slots 155 and sleeve 157. Lugs 153 within slots 155 provide a means for preventing rotation of coupling 151 within lower pressure housing 101.

Tube 159 is secured to the lower end of coupling 151. Tube 159 has wireway 160 extending therein for passing wiring through the lower most end of lower pressure housing 101 and downward to other tools which may be connected beneath fluid holdup tool 17 in a production logging tool string such as tool string 11 shown in FIG. 1. Seals 161 seal between pressure coupling 111 and tubing 159. Bearings 163 and 165 support tube 159 within slotted sleeve 115 for linear movement relative to housing 101 along a longitudinal axis of housing 101. Seal 167 seals between bull nose 117 and tube 159. As mentioned above, bull nose 117 may be replaced with a connector having a profile such as the lower end of housing coupling 99 for securing to a connector for a production logging tool run beneath fluid holdup tool 17, such as connector 103 shown in FIG. 4a.

Tube 181 extends from pressure coupling 111 and is secured to one of caliper arms 31. Tube 181 has wireway 183 extending therein for passing conductor wires to one of sensors 33 (shown in FIG. 2). Member 185 extends between tube 159 and arm 31. Arm 31 is movably connected to slotted sleeve 115 at pivot point 187. Member 185 is movably connected to arm 31 at pivot point 189. Member 185 is movably connected to tube 159 at pivot point 191 by coupling 193. Coupling 193 is threadingly secured to tube 189. Ring 195 is secured to slotted sleeve 115 and coupling 197 is secured to tube 159 with bias spring 199 disposed therebetween for biasing tube 159 to move downward and into cavity 205 of bullnose 117. Sensor sockets 207 are provided in each of arms 31 for receipt of sensors 33 (shown in FIG. 2).

Figures 4D, 4E:
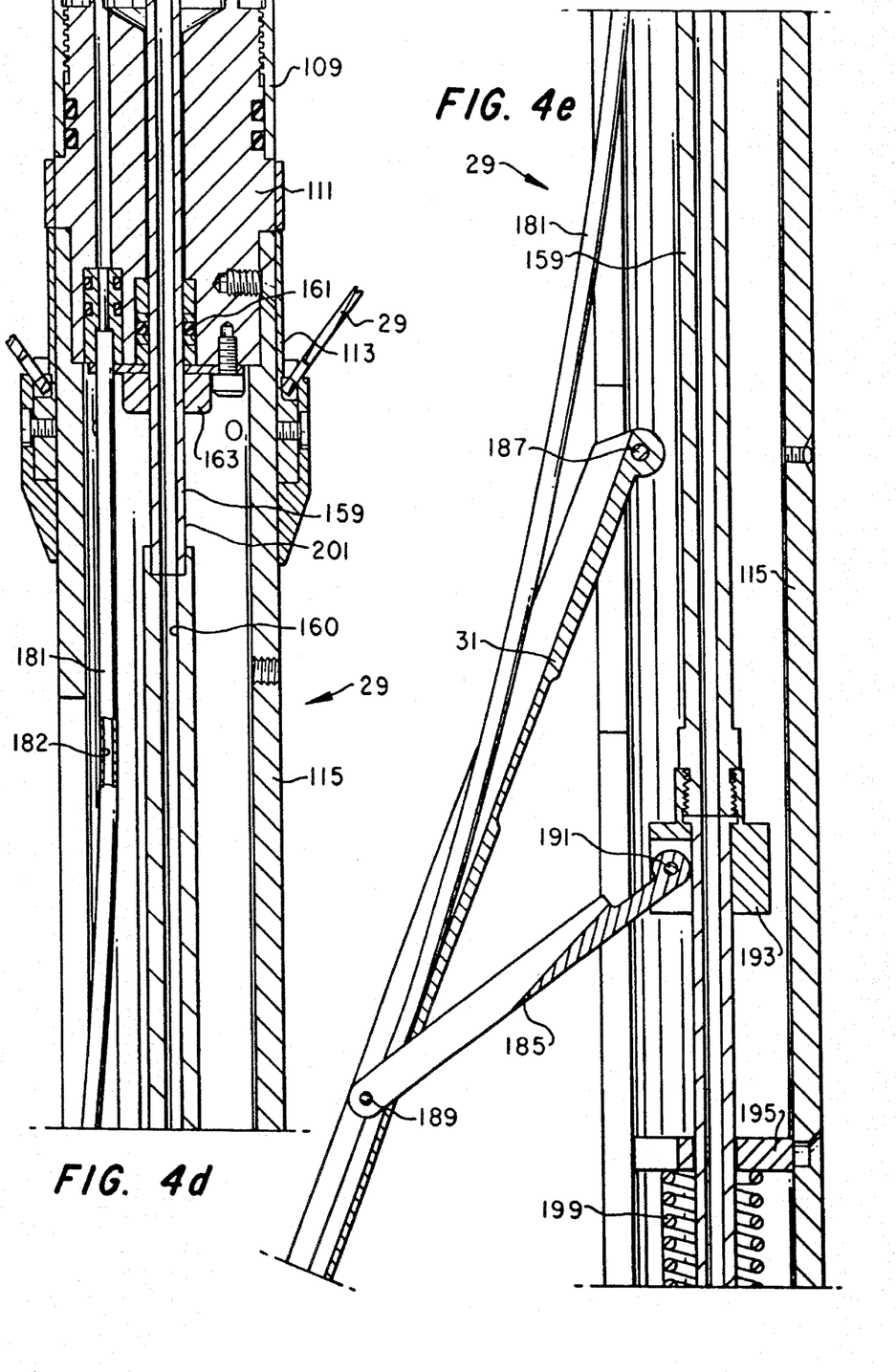
Figure 4F:
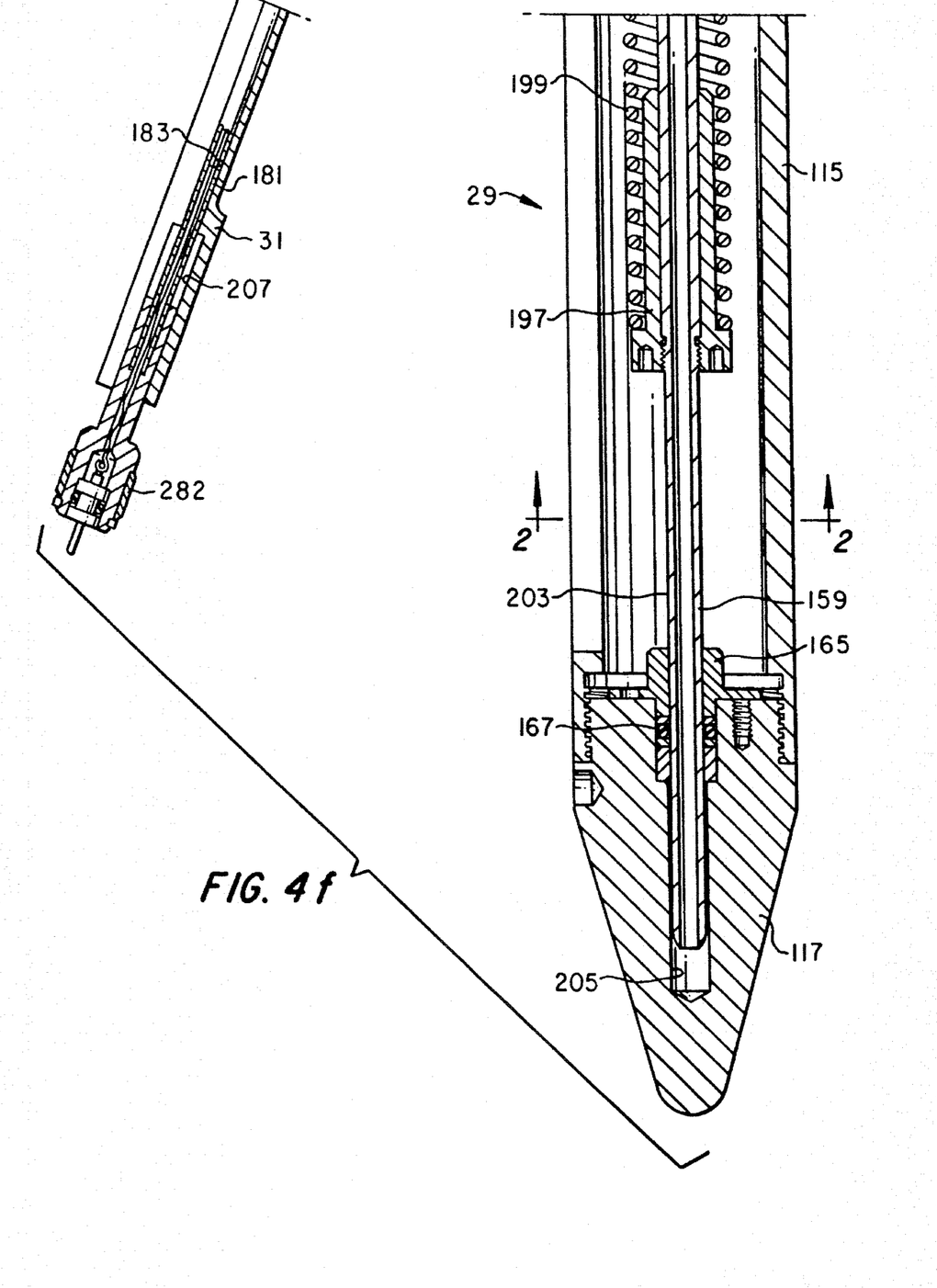

It should be noted that tube 159 is machined so that outside diameter 201, shown in FIG. 4d, is smaller than outside diameter 203, which is shown in FIG. 4f. This provides a larger cross-sectional area at outside diameter 203 than that which cross-sectional area which is defined by outside diameter 201. When exposed to well fluids, the pressure within cavity 205 of bullnose 117 is atmospheric, and the pressure within pressure sleeve 109 is also atmospheric. The difference between cross-sectional areas defined by outside diameter 201 and outside diameter 203 results in a net downward force being applied to tube 159 when exposed to downhole well pressures. For example, in the preferred embodiment of the present invention, outside diameter 201 is ten thousandths (0.010) inches smaller than outside diameter 203, which results in 80 pounds downward force at a downhole operating pressure of 20,000 pounds. Thus, the difference between outside diameters 201 and 203 provides a biasing means in addition to bias spring 199. This downward pressure results in a much smoother operating linkage over a full range of downhole pressure, which does not jerk and thus provides a much more easily moved apparatus. Further, since less force is required to urge tube 159 downwards, much smaller springs such a bias spring 199, shown in FIG. 4f, and bias spring 147, shown in FIG. 4c, may be utilized in the well logging tool of the present invention. It should also be noted that bias spring 149 provides a means by which caliper arms 31 can press against to collapse if a restriction is encountered within a well.

Figure 5:
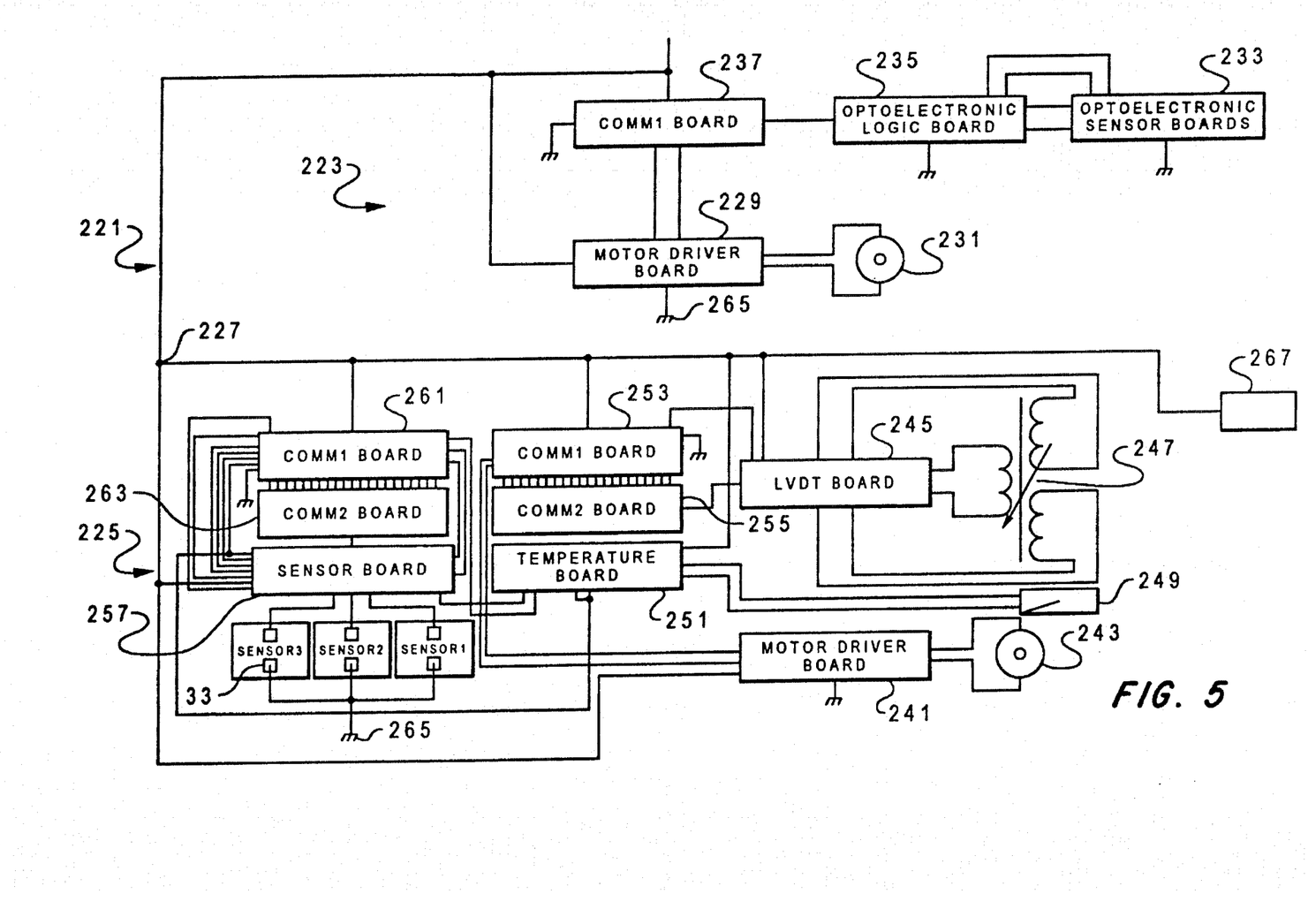
FIG. 5 is a schematic diagram depicting electronic components which are utilized for operating the fluid holdup tool in the preferred embodiment of the present invention.

With reference to FIG. 5, a schematic diagram depicts electronics 221 utilized for operating fluid holdup tool 17 of the present invention. Electronics 221 includes rotation/encoder section 223 and caliper/sensor section 225. Through wire 227 is shown extending within electronics 221. Fluid holdup tool 17 may be operated on a monocable for use in wells having high surface pressures, such as those often found on producing wells. It should be noted that through wire 227 extends through fluid holdup tool 17 for operating other downhole logging tools beneath fluid holdup tool 17.

Rotation/encoder section 223 includes motor driver board 229 and rotation motor windings 231. Rotation motor windings 231 are included within rotation motor 51 (shown in FIG. 3a). Optoelectronic sensor boards 233 and optoelectronic logic board 235 are provided for operating encoder wheels 77, L.E.D. 79, and photodiode 81 (shown in FIG. 3b). As discussed above, the optoelectronics encoder of the present invention detects angular rotation of arms 33 of fluid holdup tool 17 (shown in FIG. 2). Angular position of fluid holdup tool 17 within a well is utilized in combination with sensor readings for determining the relative volumetric proportions of fluid flow constituents flowing within the well. Communications board 237 is provided for coupling motor driver board 265 and optoelectronic logic board 235 to through wire 227 for emitting and receiving data signals.

Caliper/sensor section 225 includes motor driver board 241 which is coupled to through wire 227 for receiving power from an uphole power supply. Motor driver board 241 controls power applied to caliper motor windings 243, which are included within caliper motor 125 (shown in FIG. 4b). Linear variable differential transformer (LVDT) board 245 is coupled to LVDT components 247, which are included within LVDT assembly 141 (shown in FIG. 4c). Resistive thermonic device (RTD) sensor 249 is provided to detect the temperature of LVDT components 247 for applying temperature corrections to LVDT readings. Temperature measurement board 251 is provided for operating RTD sensor 249. Communications boards 253 and 255 are provided for passing data signals between motor driver board 241, LVDT board 245, and uphole data processing unit 267.

Fluid sensor board 257 is provided for operating sensor transducers 33. Communications board 261 and 263 are connected to fluid sensor board 257 for passing data signals between sensor board 257 and uphole data processing unit 267. In the preferred embodiment of the present invention, ground 265 is provided by tool housings 45 and 101 shown in FIGS. 3a–4f.

It should be noted that in the present invention, several types of sensors may be used within fluid holdup tool 17 for detecting volumetric proportions of fluid flow constituents. For example, sensors 33 may comprise either electrical conductivity sensors, thermal conductivity sensors, or an acoustic type of sensor. There are also other types of sensors which may be utilized in the present invention. The above three types of sensors are disclosed herein and discussed below to illustrate examples of different types of transducers which may be utilized for sensors 33.

Figure 6:
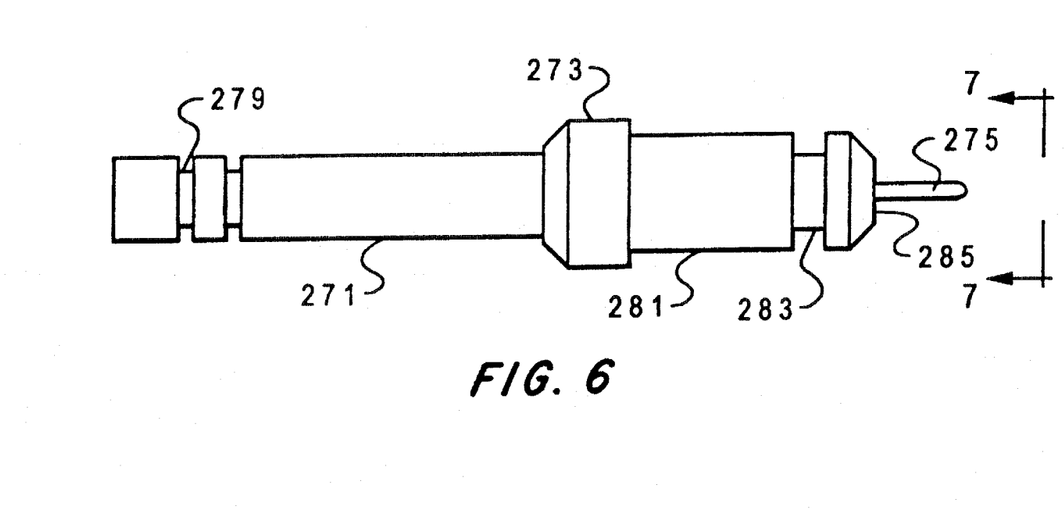
FIG. 6 is a side view of an electrical conductivity sensor for use in the fluid holdup tool of the present invention.

Referring now to FIG. 6 a side view depicts electrical conductivity sensor 271 for use as one of sensors 33 of the present invention. Sensor 271 includes conductive body 273 from which sensor pin 275 extends with an insulator material 277 extending therebetween (shown in FIG. 7). O-ring seal grooves 279 are provided within body 273. Roller bearing surface 281 is provided for receipt within roller bearing 282 (shown in FIG. 4f) for allowing body 273 to rotate within roller bearing 282 (shown in FIG. 4f). Snap ring retainer groove 283 is provided to retain body 273 within one of sockets 287. End face 285 of conductive body 273 provides a ground for current to return from sensor pin 275.

Figure 7:
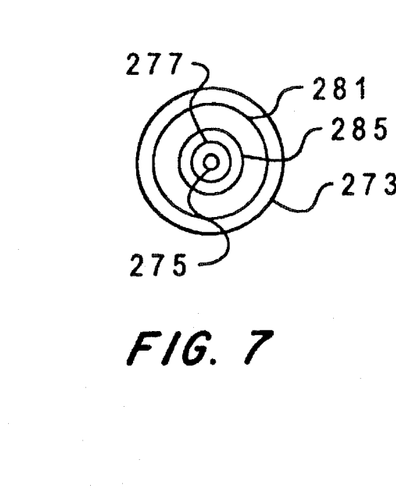
FIG. 7 is an end view of the electrical conductivity sensor of FIG. 6.
Figure 8:
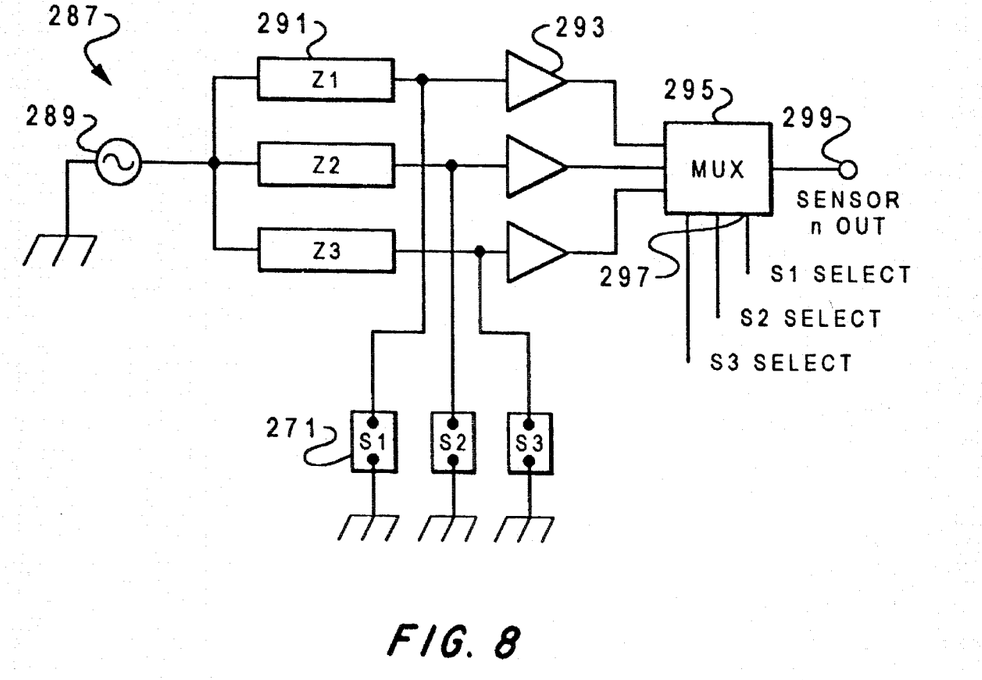
FIG. 8 is a schematic diagram depicting electronic components used for operating with the electrical conductivity sensor of FIGS. 6 and 7.

With reference to FIG. 7, an end view depicts the end of electrical conductivity sensor 271 as viewed from section 7—7 of FIG. 6. As shown therein, electrical conductivity sensor 271 includes end face 285 within which are concentrically disposed sensor pin 275 and insulator material 277. Insulator material 277 provides an insulation barrier between conductive body 273 and sensor pin 275. End face 285 provides a current ground for current to pass from sensor pin 275, through the well bore fluid between sensor pin 275 and end face 285, and into end face 285. Referring now to FIG. 8, a schematic diagram depicts sensor circuit 287 which is included within sensor board 257 (shown in FIG. 5) for operating three of electrical conductivity sensors 271. Power source 289 provides a 2 kHz power supply which provides voltage to impedances 291, sensors 271 and amplifier means 293. The amount of current passed through electrical conductivity sensors 271 determines the voltages applied to amplifier means 293. Amplifier means 293 each emit an output signal which varies in response to the conductivity of fluid components at sensors 271, and which are passed to multiplexer 295. Control signals applied to sensor select inputs 297 select between the output signals from the three different amplifier means 293 which are passed through to sensor circuit output 299. Communications boards 261 and 263 are utilized to couple sensor circuit output 299 to throughwire 227 for passing data signals uphole to data processing unit 267 (shown in FIG. 5).

Figure 9:
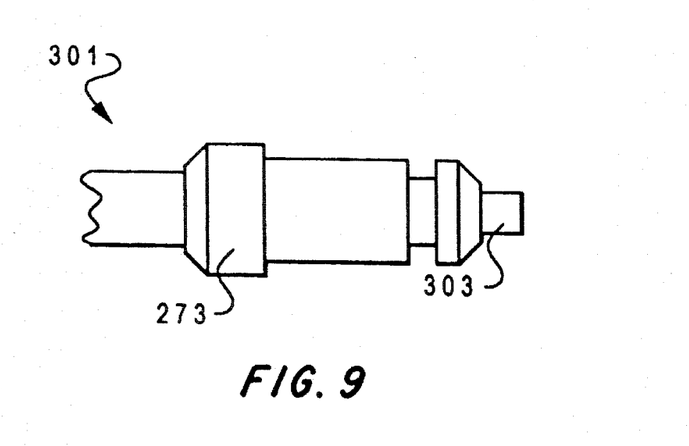
FIG. 9 is a side view of a thermal conductivity sensor for use in the present invention.

With reference to FIG. 9, a partial view depicts thermal conductivity sensor 301, three of which may be utilized for providing three sensors 33 in the present invention. Thermal conductivity sensor 301 includes RTD sensor 303, which in this embodiment of the present invention is formed from platinum. It should be noted that conductive body 273 is used for housing RTD sensor 303, as is discussed above for electrical conductivity sensor 271.

Figure 10:
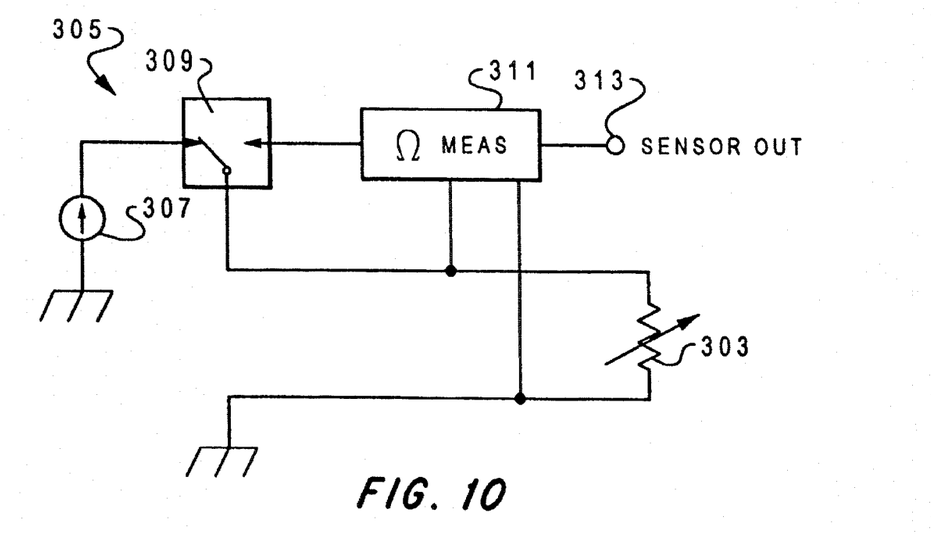
FIG. 10 is a schematic diagram depicting electrical components for operating the thermal conductivity sensor of FIG. 9.

Referring now to FIG. 10, a schematic diagram depicts sensor circuit 305 for use within fluid sensor board 257 (shown in FIG. 5). It should be noted that as depicted herein, sensor circuit 305 is for use to operate only one of sensors 301. Sensor circuit 305 includes power source 307 and switch 309. Switch 309 is selectively operated to pass current through to RTD sensor 303 for heating RDT sensor 303 to a temperature which is above the temperature of downhole well fluids within which RDT sensor 303 is immersed. Measurement circuitry 303 is provided to selectively open switch 309 and then detect the temperature decay of RDT sensor 303 after power source 307 is disconnected therefrom. Sensor circuit output 313 corresponds to the rate of the temperature of RDT sensor 303. Measurement circuitry 311 measures the electrical resistance of RDT sensor 303, which varies in response to temperature. The decay rate of the temperature of thermal conductivity sensor 301 is utilized to determine the thermal conductivity of fluids within which RTD sensor 303 is emerged.

Figure 11:
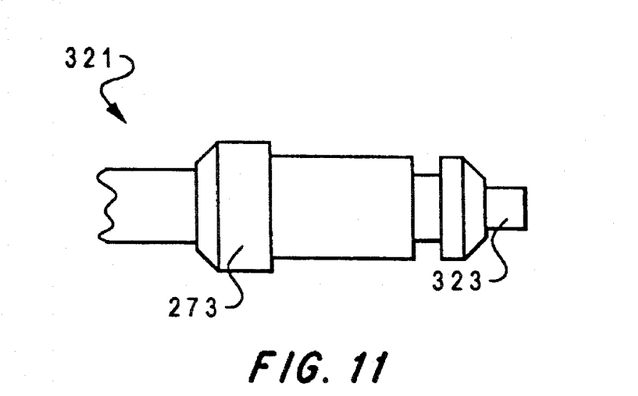
FIG. 11 is a side view depicting an acoustic piezoelectric sensor for use in the present invention.

With reference to FIG. 11, a partial view depicts acoustic sensor 321, which may be utilized to provide sensors 33 of the preferred embodiment of the present invention. Acoustic sensor 321 includes conductive body 273. Piezoelectric element 323 extends from body 321 for passing acoustic energy to well fluids within which piezoelectric element 323 is immersed. Piezoelectric element 323 of this embodiment of the present invention is sized so that it is adapted for use to emit acoustic energy at a frequency of approximately 500 kHz.

Figure 12:
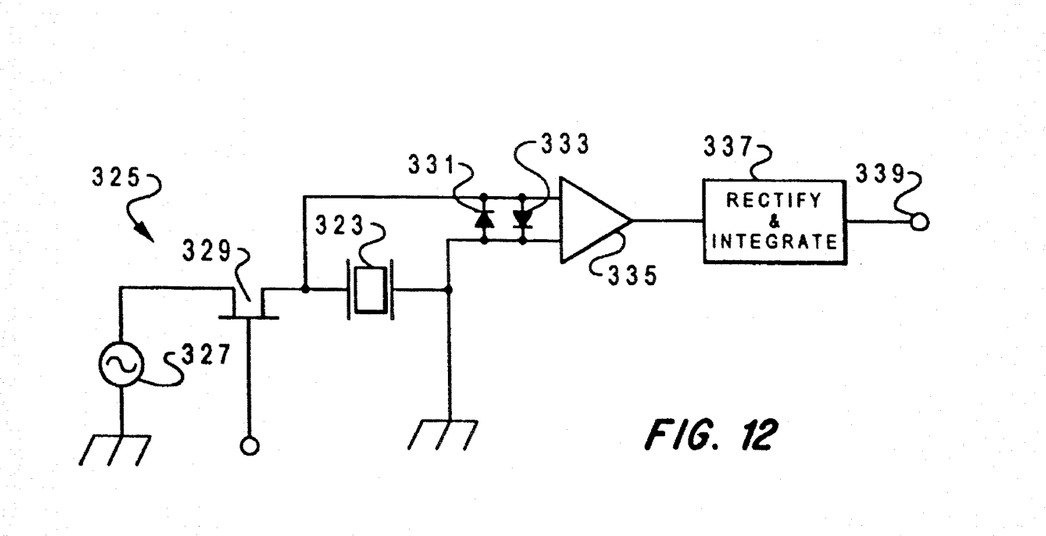
FIG. 12 is a schematic diagram depicting electronic components for operating the acoustic sensor of FIG. 11.

Referring now to FIG. 12, a schematic diagram depicts sensor circuit 32S for use within fluid sensor board 257 (shown in FIG. 5), for operating one of acoustic sensors 321. It should be noted that if three of acoustic sensors 321 are utilized in a fluid holdup tool 17 of the preferred embodiment of the present invention, three of sensor circuits 325 will be required. Sensor circuit 325 includes power source 327 for operating piezoelectric element 323 at a frequency of approximately 500 kHz. Firing signal gate 329 is provided by a field effect transistor for selectively applying power from power source 327 to element 323. One terminal end of piezoelectric element 323 is connected to ground, and the other is connected to amplifier means 335 with diodes 331 and 333 bridging therebetween as shown. The output from amplifier means 335 passes to rectifier and integrator means 337 which emits a data signal on sensor circuit output 339 in response thereto. Sensor circuit 325 operates to selectively pass a pulse of electrical energy through firing signal gate 279 and to piezoelectric element 323. A sharp pulse of electrical energy applied to piezoelectric element 323 causes resonance frequency vibrations within element 323. As discussed above, piezoelectric element 323 in this embodiment of the present invention is sized so that an acoustic signal of approximately 500 kHz is emitted. The rate of decay of the acoustic signal emitted from piezoelectric element 323 will vary depending on the well fluid within which element 323 is immersed. The resonance vibrations within piezoelectric element 323 cause a voltage to be applied to amplifier means 335, which emits an output signal in response thereto for passing to rectifier integrator means 337, which in turn emits a data signal to sensor circuit output 339.

Figure 13:
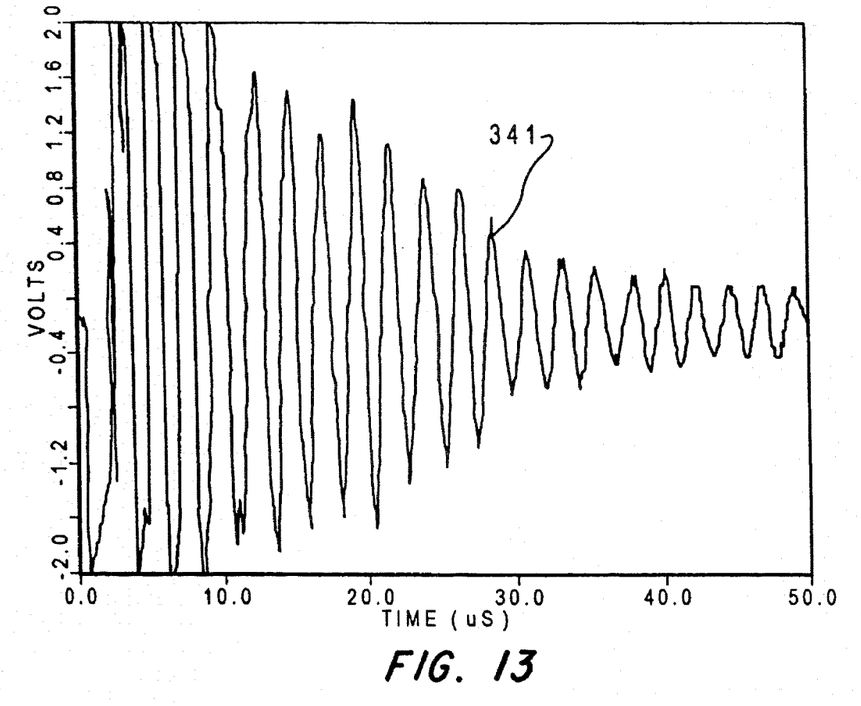
FIG. 13 is a graph which depicts the electrical response characteristics of the acoustic sensor of FIG. 11 when immersed in gas.
Figure 14:
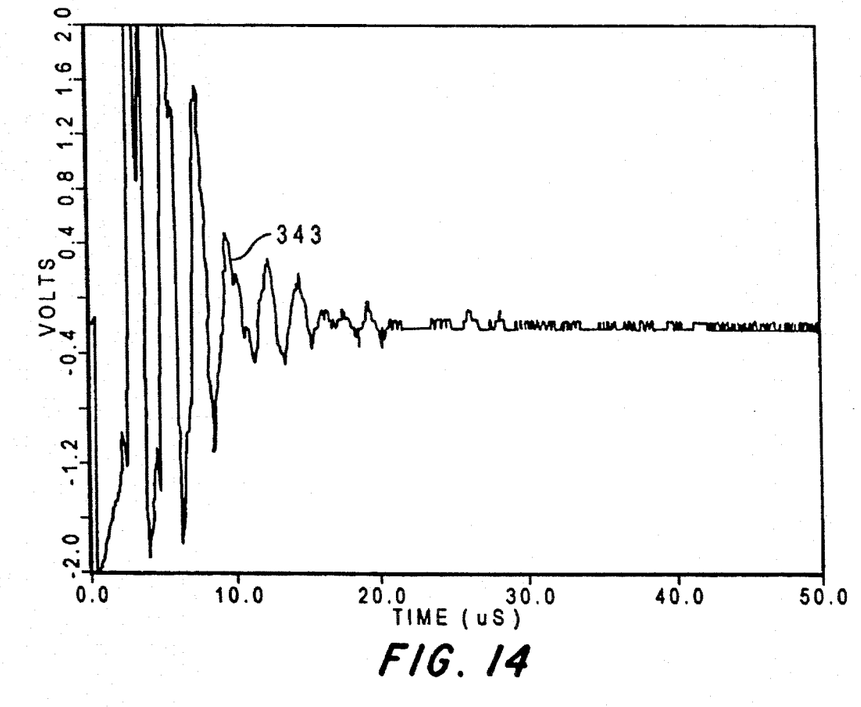
FIG. 14 is a graph which depicts the electrical response characteristics of the acoustic sensor of FIG. 11 when immersed in water.

With reference to FIGS. 13 and 14, graphs of voltage versus time depict operational characteristics of acoustic sensor 321 of FIGS. 11 and 12. Curve 341 of FIG. 13 is a plot of the output voltage from piezoelectric element 323 which occurs in response to dampening of the resonance vibrations. In particular, curve 341 depicts the output voltage of element 323 when immersed in gas.

Curve 343 in FIG. 14 depicts the output voltage from piezoelectric element 323 when immersed in water. As seen by comparison of curves 341 and 343, water is capable of transmitting much more acoustic energy over a particular period of time than gas, so the resonance frequency vibrations within piezoelectric element 323 are dampened much more quickly when element 323 is immersed in water rather than gas. It should also be noted, that the rate of attenuation from "an oil or oil emulsion" would be intermediate of that between curve 341 and 343.

Fluid holdup tool 17 of the present invention may be used with three of either electrical conductivity sensors 271, thermal conductivity sensor 301, or acoustic sensor 321. Additionally, fluid holdup tool 17 in the present invention may be used with any combination of the above sensors, including other sensors which are not specifically mentioned herein. This can easily be accomplished by providing different fluid sensor boards 257 (shown in FIG. 5) which are tailored for the combination of sensors desired for use within fluid holdup tool 17.

Operation of fluid holdup tool 17 of the present invention is now described. Referring now to FIGS. 3a–3c, and FIG. 4a–4f, once fluid holdup tool 17 is lowered within a well, caliper motor 125 is operated to rotate worm gear 135 so that tube 159 is moved towards the lower end of tool 17. This urges caliper arms 31 to extend radially outward from slotted housing 115. LVDT 141 determines relative movement of coupling 151. Centralizers 29 center fluid holdup tool 17 within the well, and prevent upper pressure housing 45 from rotating within the well.

Rotator motor 51 then rotates shaft 83 which is coupled to housing coupling 99 for rotation therewith. Housing coupling 99 is coupled to the lower pressure housing 101 to urge pressure housing 101 to rotate within centralizer 209. Referring to FIG. 2, this urges arms 131 to rotate within well fluids 39, and 41, which moves sensors 33 therein. Referring to FIG. 3b, rotary encoder section 61 detects angular rotation of shaft 83, and thus arms 36, with respect to upper pressure housing Upper pressure housing 45 is held in place within the well by centralizers 29, which are depicted in FIG. 1. It should be noted that in the preferred method of operation stationary readings are taken. However, fluid holdup tool 17 may be utilized to provide a well log while being moved within a well. If stationary readings are taken, but rather the fluid holdup tool is being moved within a well on a wireline, it would be advantageous for well log analysis to include a device to detect the angular position of holdup tool 17 with respect to either the high or low side of the hole, or a gyroscope type device for detecting total angular movement of upper section 27 of fluid holdup tool 17 for processing data.

With reference to FIG. 5, electronics section 221 controls downhole operation of fluid holdup tool 17. Commands from uphole data processing unit 267 are passed downhole via throughwire 227 to communication board 253 for controlling operation of caliper motor 125. Communication board 253 is connected to motor driver board 241 for determining when arms 31 are extended radially outward or retracted radially inward. It should be noted that when arms 31 are extended radially outward, they still may be pressed inward when restrictions are encountered as discussed above. LVDT 141 detects the extent of radial extension of arms 31. RTD 249 detects the temperature within LVDT 141. Communication board 253 emits a data signal through wire 227 and to uphole data processor 267 in response to output signals from LVDT board 245. Sensor board 257 is coupled to throughwire 227 for providing power for operating both sensor board 257, and sensors 33. Sensor board 257 emits a data signal through wire 227 to uphole data processor 267 in response to output signals from sensor 33 and temperature board 251, which detects the temperature within LVDT 141. Operation of three particular sensors which may be utilized for sensors 33 in this preferred embodiment of the present invention are discussed above in reference to FIGS. 6–14.

Communication board 237 is connected to throughwire 227 for receiving command signals from data processor 267. Communication board 237 emits control signals to motor driver board 265 to control the power applied to windings 231 for controlling operation of rotation motor 51 in response thereto. Optoelectronic logic board 235 and optoelectronic sensor board 233 provides power to LED 79 and photodiode 81 for controlling operation thereof (shown in FIGS. 3a and 3b). Rotation of encoder wheel 77 passes slots in wheel 77 between LED 79 and photodiode 81 which causes light to be pulsed to photodiode 81. Photodiode 81 emits electrical pulses in response to the light pulses emitted by LED 79. The electric pulses from photodiode 81 are detected by optoelectronic sensor board 233. Optoelectronic sensor board 233 and optoelectronic logic board 235 are coupled to communication board 237, which emits a data signal which corresponds to the angular rotation of encoder wheel 77. The data signal from communication board 237 is coupled to throughwire 227 for passing uphole to data processing unit 267.

Data processing unit 267 is then utilized for processing the different output signals passed uphole from communication boards 237, 261 and 253 to determine volumetric proportions of flow constituents within a fluid flow stream as sensors 33 are rotated within the flow stream. Data from fluid holdup tool 17 is analyzed along with data from density tool 19, deflector flowmeter 21, and fullbore flowmeter 23 for determining the different flow rates of fluid flow constituents within a well when fluid holdup tool 17 is utilized in combination with a full assembly of production logging tools in a producing well. It should be noted that fluid holdup tool 17 may be run without other production logging tools.

Referring again to FIG. 2, it should be noted that as sensors 33 are rotated within a flowstream such as that shown therein, each sensor will emit a periodic signals when passing between brine 37, oil 39 and gas 41. Thus, unlike prior art devices, fluid holdup tool 17 of the preferred embodiment of the present invention may be utilized within deviated or even horizontal wells for detecting the volumetric proportions of the different flow constituents such as brine 37, oil 39, and gas 41. It should also be noted that fluid holdup meter 17 of the present invention may also be utilized for analyzing segregated and segmented fluid flow in other applications such as vertical, or for non-deviated wells, or detecting flow through surface pipes. Further, logging readings may be recorded without operating rotation motor 151.

After logging readings are recorded, rotation motor 151 may be stopped, and caliper motor 125 may be operated to retract arms 131 radially inward for removal of tool string 11 from the well.

The present invention offers several advantages over prior art fluid holdup tools. Sensors are secured within caliper arms which extend radially outward from the tool housing to points which are spaced apart from a tool housing to detect volumetric proportions of fluid flow constituents. Thus, fluid holdup may be determined without relying upon data acquired from only a central portion of the well. Additionally, sensors are rotated about a longitudinal axis of the flowpath through a well for passing around the edge exterior of a cross-sectional area of the flow for much more accurately determining flow parameters. Since sensors are rotated about a longitudinal axis of the well, the fluid holdup tool of the present invention may be used in deviated, and even horizontal wells, since they will each pass through the different flow constituents rather than just detecting the flow components within a particular portion of a cross-sectional area of the well.

Although the invention has been described with reference to specific embodiments, this description is not meant to be construed in a limiting sense. Various modifications of the disclosed embodiments as well as other alternative embodiments of the invention will become apparent to persons skilled in the art upon reference to the description of the invention. It is therefore contemplated that the appended claims will cover any such modifications or embodiments that fall within the true scope of the invention.

We claim:

1. A production logging tool for use in a tool string to determine fluid holdup of a multiphase fluid flow within a well, said production logging tool comprising:

a tool housing having a power supply and an electronics section disposed therein;

a plurality of arms rotatably mounted to said tool housing, each of said plurality of arms extending from said tool housing to points distal from a longitudinal axis of said tool housing, wherein said distal points are spaced apart along a satellite path which circumscribes said tool housing;

a motor for rotating said plurality of arms about said tool housing to pass said plurality of sensors through said satellite path which circumscribes said tool housing for detecting said variations in said fluid property;

an angular position detector for indicating an angular position of said plurality of arms about said tool housing, which determines said angular position for said points at which said plurality of sensors detect said variations in said fluid property;

a mechanical power source for selectively controlling said distal spacing between said plurality of arms and said tool housing;

a spacing detection means for indicating said distal spacing of each of said points from said tool housing; and a plurality of sensors for detecting variations in a fluid property attributable to different flow constituents of said multiphase fluid flow, wherein each of said plurality of sensors is secured to one of said plurality of arms at one of said points and exposed to said multiphase fluid flow within said well for determining proportions of said different flow constituents at each of said points.

2. The production logging tool of claim 1, wherein said arms are angularly spaced around said longitudinal axis of said tool housing, separated by proximately equal angular displacements.

3. The production logging tool of claim 1, wherein said fluid property is electrical conductivity of said different flow constituents of said multiphase fluid flow, and said plurality of sensors comprises:

electrical probes for disposing at said points, which are disposed at ends of said arms, and passing a current therethrough for detecting said electrical conductivity of said different flow constituents.

4. The production logging tool of claim 1, wherein said fluid property is thermal conductivity of said flow constituents of said multiphase fluid flow, and wherein said plurality of sensors comprises:

resistive elements which change in resistivity in response to changes in temperature;

a power source for passing electrical current through said resistive elements to raise a temperature of said resistive elements above a well temperature of said different flow constituents; and detection means that determine the proportions of various flow constituents at each of the plurality of points in accordance with such measured resistivity changes at the plurality of sensors, and with means for emitting a data signal which varies in response to said resistivity of said resistive element.

5. The production logging tool of claim 1, wherein the sensors are disposed on the ends of the plurality of arms.

6. A production logging tool for use in a tool string to determine fluid holdup of a multiphase fluid flow within a well, said production logging tool comprising:

a tool housing having a power supply and an electronics section disposed therein;

a plurality of arms, each of said plurality of arms extending from said tool housing to a point distal from said tool housing, wherein said points are spaced apart along a path which circumscribes said tool housing;

a plurality of sensors for detecting variations in a fluid property attributable to different flow constituents of said multiphase fluid flow, wherein each of said plurality of sensors is secured to one of said plurality of arms at one of said points for determining proportions of said different flow constituents at each of said points;

wherein said fluid property corresponds to a rate of sonic attenuation of a vibrations within said plurality of sensors when exposed to said different flow constituents, and wherein said plurality of sensors comprises:

means for emitting an electrical pulse;

piezoelectric crystals which are exposed to said different flow constituents and excited by said electrical pulse which induces said vibrations therein, and wherein said piezoelectric crystals emit different voltage potentials in response to said vibrations to changes in said vibrations and said sonic attenuation of sensor vibrations while acoustically coupled to said different flow constituents; and means for detecting said voltage potential and emitting an output data signal in response thereto.

7. The production logging tool of claim 1, wherein each of said plurality of arms is rotatably mounted to said tool housing, and separated by proximately equal angular displacements, and wherein said production logging tool further comprises:

a motor for rotating said plurality of arms about said tool housing to pass said plurality of sensors through said path which circumscribes said tool housing for detecting said variations in said fluid property;

an angular position detector for indicating angular positions of said plurality of arms about said tool housing, which determines said angular position for said points;

a mechanical power source for selectively controlling said distal spacing between said plurality of arms and said tool housing; and a spacing detection means for determining said distal spacing of each of said points from said tool housing.

8. A production logging tool for use in a tool string to determine fluid holdup of a multiphase fluid flow within a well, said production logging tool comprising:

a tool housing having a power supply and an electronics section disposed therein;

centralizer means for disposing said tool housing within a central region of said well;

at least one arm extending from said tool housing to a point distal from said tool housing, said at least one arm rotatably mounted for moving said point to circumscribe a satellite path about a longitudinal axis of said tool housing;

at least one sensor secured to said at least one arm at said point for detecting variations in a fluid property attributable to different flow constituents of said multiphase fluid flow;

an angular position detection means for indicating an angular position of said at least one arm about said tool housing, which determines said angular position at which said at least one sensor detects said variations in said fluid property;

a motor for rotating said at least one arm to pass said at least one sensor through said satellite path which circumscribes said tool housing, wherein said at least one sensor detects said variations in said fluid property for determining proportions of said different flow constituents disposed along said path which circumscribes said tool housing;

a spacing detection means for indicating said distal spacing of each of said points from said tool housing;

a mechanical power source for selectively controlling said distal spacing between said at least one arm and said tool housing; and wherein said motor and said mechanical power source are selectively operated to position said sensor at selected positions along said satellite path for substantially determining the proportions of said different flow constituents across a cross-sectional area of said well.

9. The production logging tool of claim 8, further comprising:

two additional arms which extend from said tool housing to two additional points which are distal from said tool housing;

two additional sensors secured to said two additional arms for detecting said variations in said fluid property at said two additional points; and wherein said two additional arms are spaced apart about said tool housing at proximately equal angles about a longitudinal axis of said tool housing from said at least one arm and are rotatably mounted for moving said two additional points about satellite paths which circumscribes said tool housing.

10. The production logging tool of claim 8, wherein said motor is an electric moto.

11. A production logging tool for use in a tool string to determine fluid holdup of a multiphase fluid flow within a well, said production logging tool comprising:

a tool housing having a power supply and an electronics section disposed therein;

centralizer means for disposing said tool housing within a central region of said well;

at least one arm extending from said tool housing to a point distal from said tool housing, said at least one arm rotatably mounted for moving said point to circumscribe a path about said tool housing;

at least one sensor secured to said at least one arm at said point for detecting variations in a fluid property attributable to different flow constituents of said multiphase fluid flow;

a motor for rotating said at least one arm to pass said at least one sensor through said path which circumscribes said tool housing, wherein said at least one sensor detects said variations in said fluid property for determining proportions of said different flow constituents disposed along said path which circumscribes said tool housing;

means for selectively extending said at least one arm a distal spacing from said tool housing, and having means that provide an adjustable, variable and controllable radial arm-length;

means for detecting said distal spacing in which said at least one arm is radially disposed from said tool housing;

means for detecting an angular displacement of said at least one sensor about a longitudinal axis of said tool housing; and means for controlling downhole operation of said production logging tool, and for processing data signals emitted from said production logging tool to determine said fluid holdup for said multiphase fluid flow within said well.

12. A production logging tool for use in a tool string to determine fluid holdup of a multiphase fluid flow within a well, said production logging tool comprising:

a tool housing having a power supply and an electronics section disposed therein;

centralizer means for disposing said tool housing within a central region of said well;

at least one arm extending from said tool housing to a point distal from said tool housing, said at least one arm rotatably mounted for moving said point to circumscribe a path about said tool housing;

at least one sensor secured to said at least one arm at said point for detecting variations in a fluid property attributable to different flow constituents of said multiphase fluid flow;

a motor for rotating said at least one arm to pass said at least one sensor through said path which circumscribes said tool housing, wherein said at least one sensor detects said variations in said fluid property for determining proportions of said different flow constituents disposed along said path which circumscribes said tool housing;

wherein said at least one arm is selectively extendable and selectively retractable in response to remote commands from a data processing unit at a ground surface of said well.

13. A production logging tool for use in a tool string to determine fluid holdup of a multiphase fluid flow within a well, said production logging tool comprising:

a tool housing having a power supply and an electronics section disposed therein;

centralizer means for disposing said tool housing within a central region of said well;

at least one arm extending from said tool housing to a point distal from said tool housing, said at least one arm rotatably mounted for moving said point to circumscribe a path about said tool housing;

at least one sensor secured to said at least one arm at said point for detecting variations in a fluid property attributable to different flow constituents of said multiphase fluid flow;

a motor for rotating said at least one arm to pass said at least one sensor through said path which circumscribes said tool housing, wherein said at least one sensor detects said variations in said fluid property for determining proportions of said different flow constituents disposed along said path which circumscribes said tool housing;

a linear differential variable transformer for detecting a distal spacing in which said at least one arm is radially disposed from said tool housing;

a caliper motor for extending said at least one arm said distal spacing from said tool housing;

biasing means for urging said at least one arm to extend radially from said tool housing to said distal spacing, wherein said biasing means yields in response to a restriction within said well urging said at least one arm to move radially inward toward said tool housing;

an optical encoder for detecting rotation of said at least one arm about a longitudinal axis of said tool housing to indicate an angular displacement of said at least one sensor with respect to said longitudinal axis of said tool housing; and an uphole data processing unit for controlling downhole operation of said production logging tool, and for processing data signals emitted from said production logging tool to determine said fluid holdup for said multiphase fluid flow within said well.

14. A method for logging a well to determine fluid holdup of a multiphase fluid flow within said well, said method for logging a well comprising the steps of:

providing a well logging tool with at least one sensor distally spaced from a tool housing at selectable distances and rotatable around said tool housing for detecting variations in a fluid property attributable to different flow constituents of said multiphase fluid flow at a plurality of points which are distal to and disposed laterally aside of the tool housing for said well logging tool;

disposing said well logging tool in said well, within said multiphase fluid flow;

selectively positioning the at least one sensor laterally aside of the tool housing at the selectable distances at said plurality of points which are angularly spaced around a longitudinal axis of said tool housing;

detecting said fluid property at said plurality of points which are laterally aside of and distal from said tool housing, wherein at least part of said plurality of points are radially disposed from and angularly displaced about a longitudinal axis of said well for detecting said fluid property substantially across a cross-sectional area of said well;

emitting data signals in response to detecting said fluid property detected at said plurality of points;

transmitting said data signals to a data processor; and processing said data signals to determine proportions of said different flow constituents disposed at said plurality of positions, substantially across said cross-sectional area of said well.

15. The method of claim 14, further comprising the steps of:

providing said production logging tool with an arm which is rotatably mounted to radially extend according to an adjustable, variable and controllable radial length from said tool housing and to which a sensor is mounted to dispose said sensor laterally aside of and distal from a longitudinal axis of said tool housing for detecting said fluid property; and rotating said arm to move said sensor about said tool housing to detect said fluid property at said plurality of points.

16. The method of claim 14, further comprising the steps of:

providing said production logging tool with a plurality of arms which radially extend from a longitudinal axis of said tool housing and a plurality of sensors for detecting said fluid property; and securing said plurality of sensors to said plurality of arms to dispose said sensors laterally aside of and distal from said tool housing, wherein said sensors are spaced apart along a path which circumscribes said tool housing for emitting said data signals in response to detecting said fluid property at said plurality of points.

17. The method of claim 14, further comprising the steps of:

providing said production logging tool with three arms which are rotatably mounted to radially extend laterally aside from a longitudinal axis of said tool housing for said production logging tool and mounted with means that provide an adjustable, variable and controllable radial length, wherein said three arms are angularly spaced proximately equal angular distances apart around said tool housing;

securing three sensors to said three arms for detecting said fluid property at said plurality of points, wherein each of said three sensors is secured to one of said three arms to angularly space said three sensors proximately said equal angular distances apart around said tool housing; and rotating said three arms around said tool housing to pass said three sensors through said plurality of points for detecting said fluid property at said plurality of points and emitting said data signals in response thereto.

* * * * *